United States Patent [19]

Carr

[11] 4,240,421

[45] Dec. 23, 1980

[54] SYRINGE SHIELD FOR RADIOACTIVE MATERIALS

[76] Inventor: James R. Carr, 2843 Aquarius Ave., Silver Spring, Md. 20906

[21] Appl. No.: 52,436

[22] Filed: Jun. 26, 1979

[51] Int. Cl.³ .............................................. A61B 6/00
[52] U.S. Cl. ..................................... 128/215; 128/1.1
[58] Field of Search ........................ 128/1.1, 215, 654; 250/506

[56] References Cited

U.S. PATENT DOCUMENTS

| | | | |
|---|---|---|---|
| 3,563,239 | 2/1971 | Hill | 128/215 |
| 3,820,541 | 6/1974 | Langan | 128/654 X |
| 4,040,419 | 8/1977 | Goldman | 128/1.1 |
| 4,060,073 | 11/1977 | Collica et al. | 128/654 X |
| 4,062,353 | 12/1977 | Foster et al. | 128/1.1 |

Primary Examiner—John D. Yasko

[57] ABSTRACT

A light weight syringe shield for use with syringes containing radioactive materials. The shield includes an outer shell of lead or similar gamma ray impervious material and a correspondingly configured inner shell of synthetic resinous materials. Both shells are of arcuate cross section, and extend through an arc substantially greater than 180 degrees so as to be selectively spread to enable the shield to be snapped laterally on the barrel of the syringe to be resiliently retained thereby. The shield is sufficiently long to cover that part of the barrel normally filled with the radioactive material, and it may be slid longitudinally of the barrel to permit calibration in an ion well chamber, as well as when the syringe is in use.

1 Claim, 4 Drawing Figures

SYRINGE SHIELD FOR RADIOACTIVE MATERIALS

BACKGROUND OF THE INVENTION

This invention relates generally to the field of hypodermic syringes, and more particularly to an improved barrel shield for protecting technicians administering radioactive materials to patients on a daily basis. Shields of this general type are known in the art, and the invention lies in specific constructional details which offer a number of advantages not available with conventional shielding construction.

The typical prior art shield construction widely used at the present time comprises a relatively heavy sleeve or barrel of lead or titanium having a central, longitudinal bore which accommodates the barrel of the syringe. A set screw or resilient means, or combination of the two is provided to lock the syringe within the shield, and, in the case of improved types, there is included a means for partially retracting the shield to permit dosage calibration prior to administering the contents of the syringe to the patient.

However, all of the prior art devices exhibit in varying degrees one or more of several disadvantages.

Because of the weight of the materials from which the shields are made, the prior art devices tend to be very heavy, and are bulky as well. In addition, since the shielding material is used for structural rigidity as well, considerable machining operations are necessary during fabrication, resulting in very high production costs, and consequent limited sale and distribution. Further, with use, the syringe tends to loosen within the shield, calling for periodic adjustment of the locking means.

Another difficulty lies in the fact that in many cases the shield must be removed for radioactivity dosage calibration. In the case of any retractable type, this step is unnecessary. Also, sufficient visibility is not afforded when the needle of the syringe is in the vein of the patient.

SUMMARY OF THE INVENTION

Briefly stated, the invention contemplates the provision of an improved syringe shield of the class described, in which the above mentioned disadvantages have been substantially eliminated. The device comprises an arcuate shield body of lead or other gamma ray impervious material in the order of 1 to 2 mm in thickness, which performs the shielding function. The lead shield has a curved planar configuration, and an arcuate extension substantially over 180 degrees so as to be expandable to snap over the barrel of a syringe to be thereafter slidably mounted thereon. As contrasted with the prior art devices, the body forms a sleeve of length sufficient to overlie that portion of the barrel which contains the actual dose, rather than the entire length of the barrel. Positioned upon the inner surface of the body is a thin lining of resilient non-shielding synthetic resinous material. Thus, the shield may be installed and removed readily by snapping it on or off the syringe barrel.

The shield does not wrap around the entire circumference of the syringe barrel, therefore the only person who is shielded is the technician. As the thickness of the impervious material is of a relatively low order, the reduction in weight, as contrasted with prior art devices, is considerable.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENT

Figure 1:
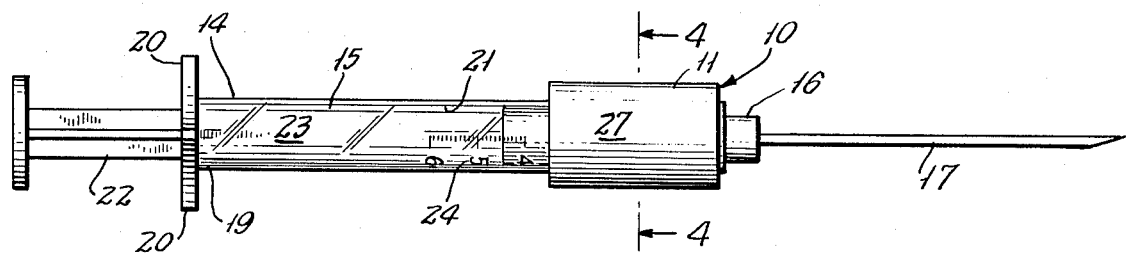
FIG. 1 is a side elevational view of an embodiment of the invention in installed position upon a known hypodermic syringe.
Figure 2:
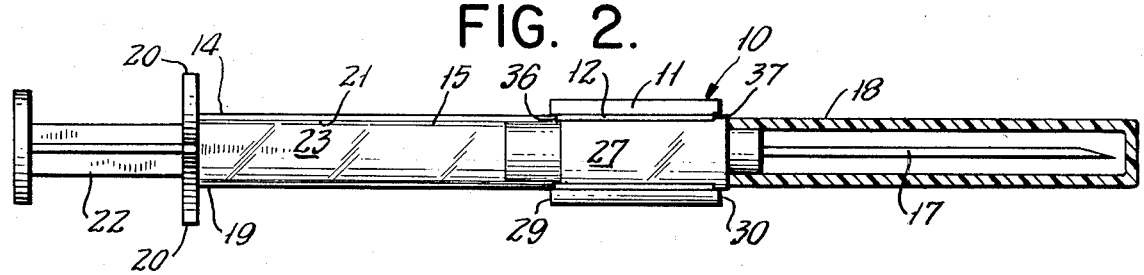
FIG. 2 is a side elevational view thereof, showing the side opposite that seen in FIG. 1.
Figure 3:
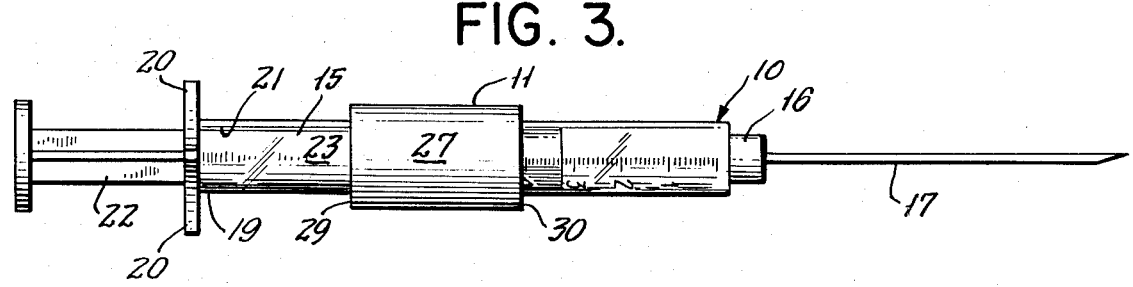
FIG. 3 is a side elevational view showing the embodiment in retracted position, as when dose calibrating, or to permit visualization of the contents during administration.

In accordance with the invention, the device, generally indicated by reference character 10, comprises broadly: an outer shielding sleeve member 11 and an inner resilient member 12.

Referring to FIG. 1 in the drawing, there is disclosed a conventional syringe 14 including an elongated barrel element 15, the lower end 16 of which is provided with a detachable needle 17 protected by a detachable needle shield 18. The upper end 19 is provided with the usual manually engageable flanges 20, and an opening to a bore 21 accommodating a slidably engageable plunger 22. The outer surface of the barrel 23 is provided with the usual calibrations 24.

Figure 4:
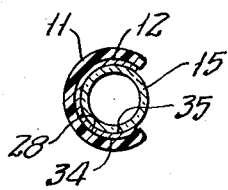
FIG. 4 is a transverse sectional view as seen from the plane 4—4 in FIG. 1.

The shielding member 11 is most conveniently formed from lead sheeting of thickness varying between 1 and 2 millimeters, and is bounded by an outer surface 27, an inner surface 28, and arcuate end surfaces 29 and 30. In the alternative, it may be formed as an extrusion which is severed at periodic intervals to form the desired length. As best seen in FIG. 4 in the drawing, the member 11 extends over an arc substantially exceeding 180 degrees, to permit it to be snapped onto and as readily removed from the outer surface 23 of the barrel element 15. The inner resilient member 12 is formed using synthetic resinous materials. It includes an outer surface 34, an inner surface 35 secured to the inner surface 28 of the member 11, as well as end edge surfaces 36 and 37 which are preferably disposed inwardly of the corresponding end surfaces 29 and 30, respectively. The members 11 and 12 are interconnected by any convenient means, as for example double surfaced pressure sensitive tape or suitable cementitious materials.

It will be observed that the device 10 is considerably shorter than the length of the barrel element 15 and can be conveniently slid therealong to expose or cover that portion of the bore 21 adjacent the needle 17. This permits the device to be conveniently exposed for dose calibration and administration.

I wish it to be understood that I do not consider the invention limited to the precise details of structure shown and set forth in this specification, for obvious modifications will occur to those skilled in the art to which the invention pertains.

I claim:

1. In combination, a hypodermic syringe having a barrel of given length, and a shield therefor protecting a user against radioactive materials carried by said barrel, said shield including a radially flexible resilient synthetic resinous inner sleeve member of arcuate cross section extending over an arc substantially greater than 180 degrees, and bounded by an inner surface of curvature corresponding to that of the outer surface of said barrel when said sleeve is in relatively unstressed condition, and being in substantial contact with the outer surface of said barrel under relatively light tension, said sleeve member having an outer arcuate surface; and an outer shield member of lead secured to said outer surface of said sleeve member of thickness ranging from one to two millimeters; said shield having an axial link substantially less than that of said given length, and being resiliently retained on said barrel for sliding movement there along.

* * * * *